(12) United States Patent
Boyd et al.

(10) Patent No.: US 9,435,669 B2
(45) Date of Patent: Sep. 6, 2016

(54) INTAKE GAS SENSOR WITH VORTEX FOR INTERNAL COMBUSTION ENGINE

(71) Applicant: Robert Bosch GmbH, Stuttgart (DE)

(72) Inventors: David Boyd, Greenville, SC (US); Craig Magera, Simpsonville, SC (US)

(73) Assignee: Robert Bosch GmbH, Stuttgart (DE)

( * ) Notice: Subject to any disclaimer, the term of this patent is extended or adjusted under 35 U.S.C. 154(b) by 283 days.

(21) Appl. No.: 13/793,129

(22) Filed: Mar. 11, 2013

(65) Prior Publication Data

US 2014/0174176 A1    Jun. 26, 2014

Related U.S. Application Data

(60) Provisional application No. 61/739,954, filed on Dec. 20, 2012.

(51) Int. Cl.
*G01D 11/24* (2006.01)
*G01N 27/407* (2006.01)

(52) U.S. Cl.
CPC ........... *G01D 11/24* (2013.01); *G01N 27/4077* (2013.01)

(58) Field of Classification Search
CPC . G01D 11/24; G01D 11/245; G01N 27/4077
See application file for complete search history.

(56) References Cited

U.S. PATENT DOCUMENTS

| 4,326,862 | A | | 4/1982 | Suzuki | |
|---|---|---|---|---|---|
| 4,507,192 | A | * | 3/1985 | Ebizawa et al. | 204/428 |
| 4,916,934 | A | * | 4/1990 | Nagata et al. | 73/31.05 |
| 5,012,670 | A | * | 5/1991 | Kato et al. | 73/31.05 |
| 5,942,092 | A | * | 8/1999 | Weyl et al. | 204/424 |
| 7,032,446 | B2 | | 4/2006 | Nakada et al. | |
| 7,493,796 | B2 | * | 2/2009 | Wilde | 73/23.31 |
| 8,001,827 | B2 | * | 8/2011 | Weyl et al. | 73/23.31 |
| 8,584,504 | B2 | * | 11/2013 | Ito et al. | 73/23.2 |
| 2002/0095916 | A1 | | 7/2002 | Turner et al. | |
| 2003/0046996 | A1 | * | 3/2003 | Nakada et al. | 73/202.5 |
| 2004/0025481 | A1 | | 2/2004 | Bugli et al. | |
| 2005/0178187 | A1 | * | 8/2005 | Nakagawa | 73/31.05 |
| 2005/0241937 | A1 | * | 11/2005 | Shichida et al. | 204/424 |
| 2008/0016946 | A1 | * | 1/2008 | Thanigachalam et al. | 73/31.05 |
| 2008/0016948 | A1 | * | 1/2008 | Yamada | 73/31.05 |

(Continued)

FOREIGN PATENT DOCUMENTS

| JP | 2001099807 | 4/2001 |
|---|---|---|
| JP | 2003161717 | 6/2003 |

OTHER PUBLICATIONS

International Search Report and Written Opinion for Application No. PCT/US2013/075327 dated Apr. 2, 2014 (11 pages).

*Primary Examiner* — Peter Macchiarolo
*Assistant Examiner* — Natalie Huls
(74) *Attorney, Agent, or Firm* — Michael Best & Friedrich, LLP

(57) ABSTRACT

A gas sensor includes a sensor housing and a sensing element located within the sensor housing. The sensing element defines an axis. The sensing element has a distal end extending from the sensor housing. The gas sensor further includes a sensor protection element coupled to the sensor housing and at least partially surrounding the distal end of the sensing element. The sensor protection element includes a tube having a conical portion, and a gas inlet located on the tube, the gas inlet spaced from the axis. The gas inlet is shaped to direct gas into the tube to induce a vortex gas flow within the conical portion of the tube.

20 Claims, 5 Drawing Sheets

(56) References Cited

U.S. PATENT DOCUMENTS

| | | | |
|---|---|---|---|
| 2008/0073209 A1* | 3/2008 | Yamada | 204/424 |
| 2008/0086989 A1 | 4/2008 | Sheidler | |
| 2008/0105037 A1* | 5/2008 | Nakashima et al. | 73/31.05 |
| 2008/0156301 A1 | 7/2008 | Rockwell et al. | |
| 2008/0277282 A1* | 11/2008 | Kume et al. | 204/424 |
| 2009/0100907 A1* | 4/2009 | Mizutani et al. | 73/31.05 |
| 2009/0117007 A1* | 5/2009 | Furuta et al. | 422/83 |
| 2009/0166358 A1 | 7/2009 | Bose | |
| 2010/0024524 A1* | 2/2010 | Ebner et al. | 73/31.05 |
| 2010/0288230 A1 | 11/2010 | McCauley et al. | |
| 2011/0114070 A1 | 5/2011 | Liu et al. | |
| 2011/0209523 A1* | 9/2011 | Otsubo et al. | 73/23.31 |
| 2012/0111092 A1* | 5/2012 | Nakashima | 73/23.31 |
| 2012/0145543 A1* | 6/2012 | Sugaya et al. | 204/424 |
| 2013/0305809 A1* | 11/2013 | Fujita et al. | 73/31.05 |
| 2014/0298931 A1* | 10/2014 | Oba et al. | 73/866.5 |
| 2014/0299469 A1* | 10/2014 | Oba et al. | 204/412 |

* cited by examiner

INTAKE GAS SENSOR WITH VORTEX FOR INTERNAL COMBUSTION ENGINE

CROSS REFERENCE TO RELATED APPLICATIONS

This application claims priority to U.S. Provisional Application No. 61/739,954, filed Dec. 20, 2012, the entire contents of which are incorporated herein by reference.

BACKGROUND

The present invention relates to a gas (e.g., oxygen) sensor, and more particularly to a gas sensor with a sensor protection element for use in low temperature environments.

The use of gas sensors to monitor oxygen levels in an internal combustion engine is known. Current gas sensors are designed for high temperature areas in the engine, such as an exhaust manifold, where the exhaust gas can reach temperatures as high as 1030 degrees Celsius. The gas sensors include sensing elements extending from sensor housings for detecting the oxygen levels of the exhaust gas.

Significant amounts of water, particles, and/or other contaminates that may damage a sensing element are not typically present in the exhaust manifolds during operation of the engine, due at least in part to the high temperatures already present in these areas. However, other areas of the engine, including the intake manifold, have significantly lower temperatures than the exhaust manifold. For example, in the intake manifold, temperatures may only reach 130 degrees Celsius. In these lower temperature areas, higher amounts of water, particles, and other contaminates are typically present, as compared with the exhaust manifold. Such water, particles, and/or other contaminants can damage and/or disrupt the sensing element. It would be advantageous therefore to have a gas sensor for use in these low temperature environments that eliminates or removes water, particles, and/or other contaminates from the gas sensor, so that the sensing element remains protected.

SUMMARY

In accordance with one construction, the invention provides a gas sensor including a sensor housing and a sensing element located within the sensor housing. The sensing element defines an axis. The sensing element has a distal end extending from the sensor housing. The gas sensor further includes a sensor protection element coupled to the sensor housing and at least partially surrounding the distal end of the sensing element. The sensor protection element includes a tube having a conical portion, and a gas inlet located on the tube, the gas inlet spaced from the axis. The gas inlet is shaped to direct gas into the tube to induce a vortex gas flow within the conical portion of the tube.

In accordance with another construction, the invention provides a gas sensor including a sensor housing and a sensing element located within the sensor housing. The sensing element defines an axis. The sensing element has a distal end extending from the sensor housing. The gas sensor further includes a sensor protection element coupled to the sensor housing and at least partially surrounding the distal end of the sensing element. The sensor protection element includes an outer tube having a conical portion. A first gas inlet is located on the outer tube. The first gas inlet is spaced from the axis. The sensor protection element further includes a waste outlet located on the conical portion. The axis extends through the waste outlet. The sensor protection element further includes an inner tube disposed within the outer tube. The sensing element is located within the inner tube. The sensor protection element further includes a second gas inlet located on the inner tube. The axis extends through the second gas inlet. The sensor protection element further includes a first gas outlet located on the inner tube. The first gas outlet is spaced from the axis. The sensor protection element further includes a second gas outlet located on the outer tube. The second gas outlet is spaced from the axis.

Other aspects of the invention will become apparent by consideration of the detailed description and accompanying drawings.

DETAILED DESCRIPTION

Figure 1:
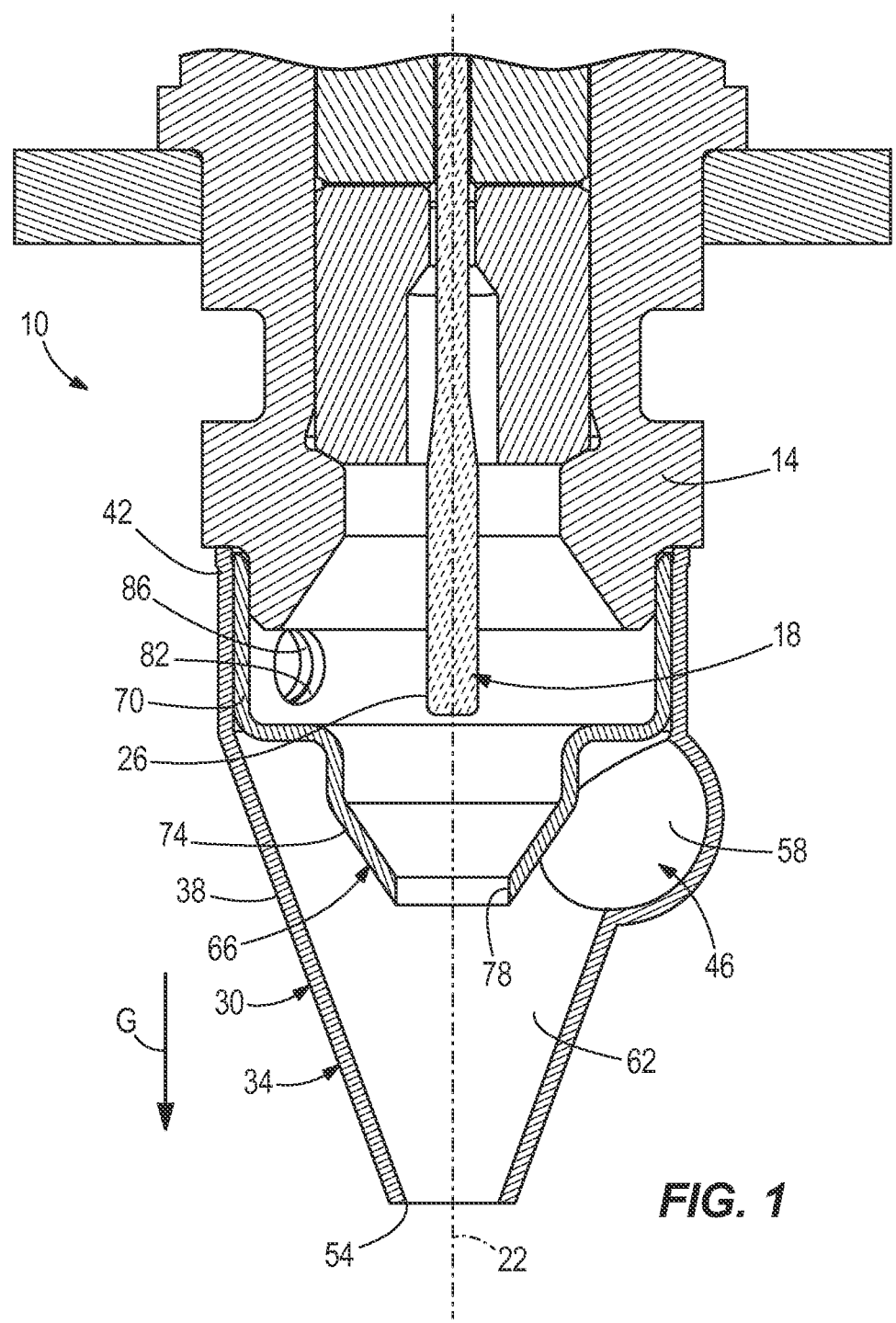
FIG. 1 is a front, cross-sectional view of a gas sensor according to one construction of the invention, the gas sensor including a sensor protection element.
Figure 3:
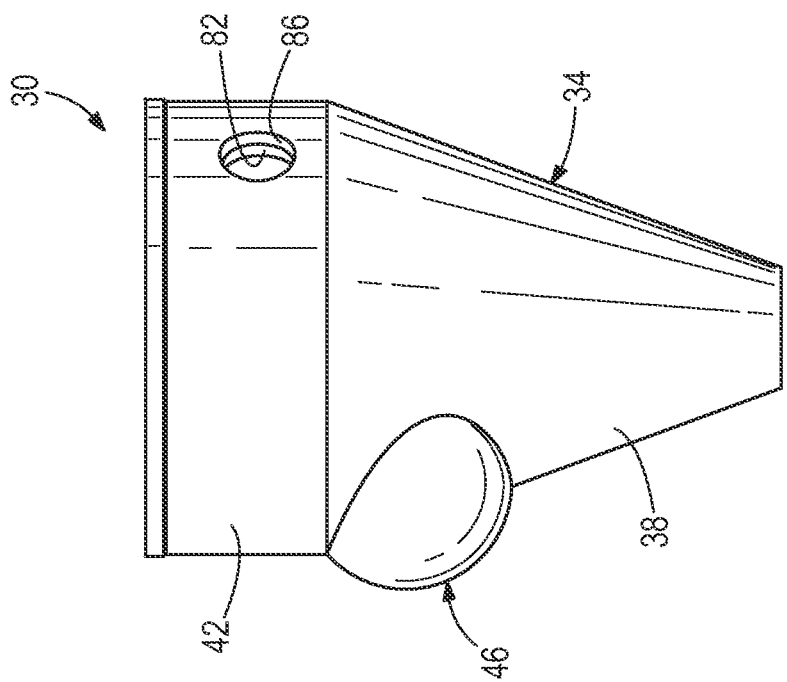
FIG. 3 is a rear view of the sensor protection element of FIG. 1.
Figure 2:
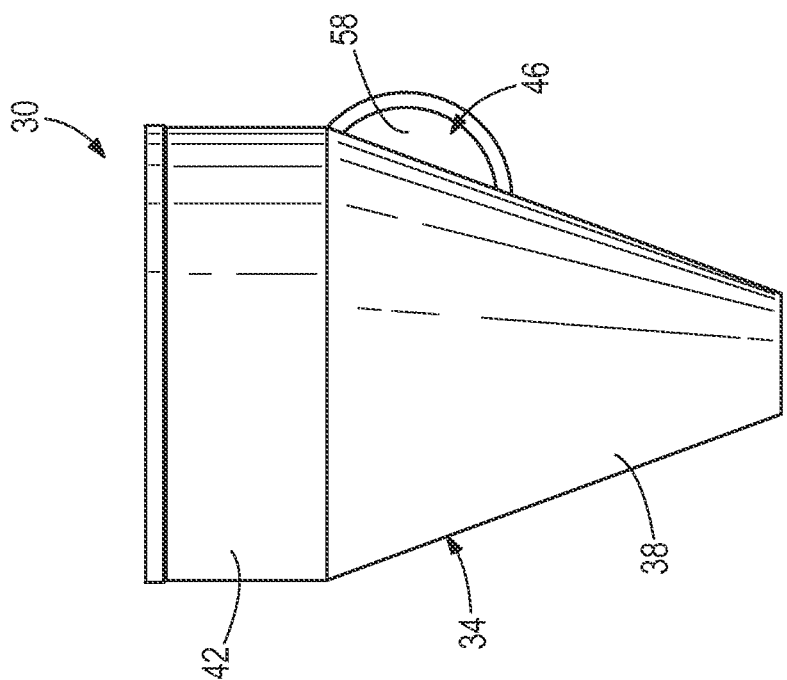
FIG. 2 is a front view of the sensor protection element of FIG. 1.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

FIGS. 1-4 illustrate a gas sensor 10. The gas sensor 10 includes a sensor housing 14, and a sensing element 18 located within the sensor housing 14. The sensing element 18 is an oxygen sensing element, although other types of sensing elements 18 are also possible. The sensing element 18 defines an axis 22. The sensing element 18 has a distal end 26 extending from the sensor housing 14. The distal end 26 extends along the axis 22.

The gas sensor 10 further includes a sensor protection element 30. The sensor protection element 30 is coupled to the sensor housing 14. Specifically, the sensor protection element 30 is coupled to the sensor housing 14 via a frictional fit over the housing 14, although other forms of coupling are also possible, including attachment with fasteners, brazing, welding, etc. The sensor protection element 30 at least partially surrounds the distal end 26 of the sensing element 18. The sensor protection element 30 controls the flow of gas from outside the gas sensor protection element 30, into communication with the sensing element 18, and back outside the sensor protection element 30.

Figure 4:
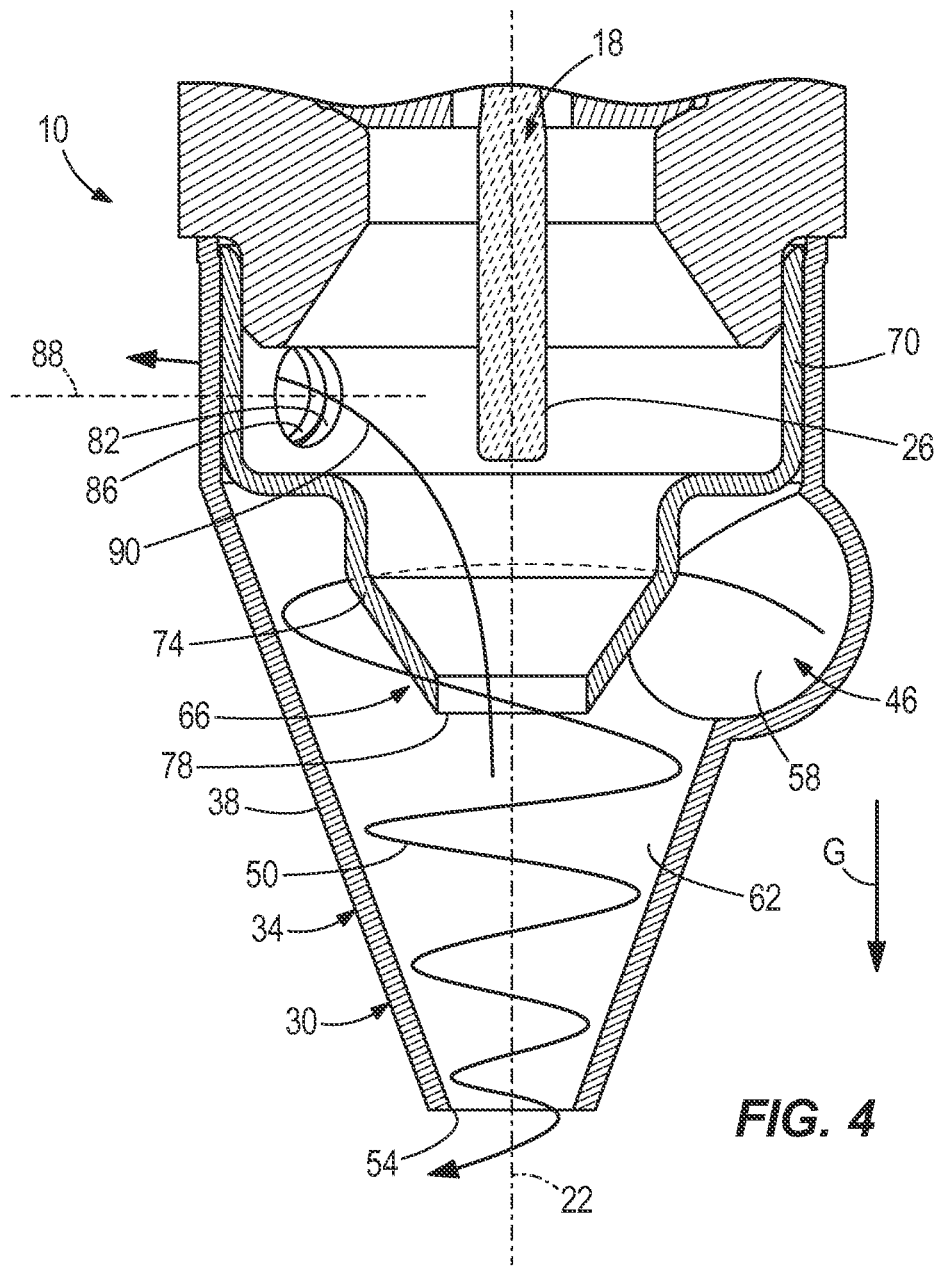
FIG. 4 is a front, cross-sectional view of the gas sensor of FIG. 1, illustrating a gas flow within the gas sensor protection element.

The sensor protection element 30 includes an outer tube 34 having a conical portion 38 and a cylindrical portion 42. A gas inlet 46 is located on the conical portion 38. The gas inlet 46 is spaced from the axis 22. The gas inlet 46 is configured to direct gas into the conical portion 38. With reference to FIG. 4, the gas inlet 46 is configured to direct gas into the conical portion 38 at an angle such that at least a portion of the gas generates into a swirling vortex 50 within the conical portion 38. The gas entering through gas inlet 46 includes water, particles, and/or other contaminates. With the aid of gravity (illustrated as arrow "G" in FIGS. 1 and 4), the swirling vortex 50 forces the water, particles, and/or other contaminants in the gas toward a waste outlet 54, and inhibits the water, particles, and/or other contaminants from reaching the sensing element 18. The waste outlet 54 is located on the conical portion 38. The axis 22 extends through the waste outlet 54.

The gas inlet 46 illustrated in FIGS. 1-4 has an outwardly facing scoop structure. The outwardly facing scoop structure extends away from the axis 22. The outwardly facing scoop structure includes an inner concave surface 58. Gas entering the gas inlet 46 moves along the inner concave surface 58 until the gas is within the conical portion 38. The conical portion 38 includes an inner surface 62. The gas entering the gas inlet 46 is directed along the inner concave surface 58, and then further along the inner surface 62. The gas inlet 46 directs gas into the conical portion 38 generally tangentially to the inner surface 62.

With continued reference to FIGS. 1-4, the sensor protection element 30 further includes an inner tube 66. The inner tube 66 is disposed within the outer tube 34. The sensing element 18 is located within the inner tube 66. Specifically, the distal end 26 of the sensing element 18 is located within the inner tube 66. The vortex 50 occurs between the outer tube 34 and inner tube 66.

The inner tube 66 includes a cylindrical portion 70, and a conical portion 74. A gas inlet 78 is located on the conical portion 74 of the inner tube 66. The axis 22 extends through the gas inlet 78. The gas inlet 78 is located generally at or below the gas inlet 46 (the terms "below" and "downward" refer to a direction along axis 22 signified by gravity arrow "G" in FIGS. 1 and 4), such that any gas that enters through gas inlet 46 must divert downward first prior to entering upward through gas inlet 78. This arrangement of the gas inlets 46, 78 creates a tortuous pathway for gas to reach sensing element 18, and further inhibits water, particles, and/or other contaminants from reaching the sensing element 18.

With continued reference to FIGS. 1-4, the inner tube 66 includes a gas outlet 82. The gas outlet 82 is spaced from the axis 22. The gas outlet 82 is located on the cylindrical portion 70 of the inner tube 66. The gas outlet 82 is disposed on a substantially opposite side of the gas sensor protection element 30 as the gas inlet 46.

The outer tube 34 further includes a gas outlet 86. The gas outlet 86 is spaced from the axis 22. The gas outlet 86 is located on the cylindrical portion 42 of the outer tube 34. The gas outlet 86 is aligned with the gas outlet 82 along an axis 88 that extends perpendicular to axis 22, such that gas within the inner tube 66 is able to move directly from within the inner tube 66 out through the outer tube 34. In the illustrated construction, the gas outlets 82, 86 have the same diameter, although other shapes and configurations for gas outlets 82, 86 are also possible.

As illustrated in FIG. 4, the gas inlet 46 admits and directs gas into the outer tube 34 in a tangential direction to induce the vortex flow 50. Water, particles, and/or other contaminants are driven to the inner wall surface 62 of the outer tube 34 by centrifugal force, and ultimately out through the waste outlet 54. This arrangement inhibits water, particles, and/or other contaminants from reaching the sensing element 18. Thus, only clean gas, denoted by line 90, is admitted into the inner tube 66 through the gas inlet 78. Once the clean gas 90 flows past the sensing element 18, the clean gas 90 exits the gas sensor protection element 30 through the gas outlets 82, 86. Negative pressure is developed by the gas outlets 82, 86, thereby facilitating the gas flow illustrated in FIG. 4.

Figure 6:
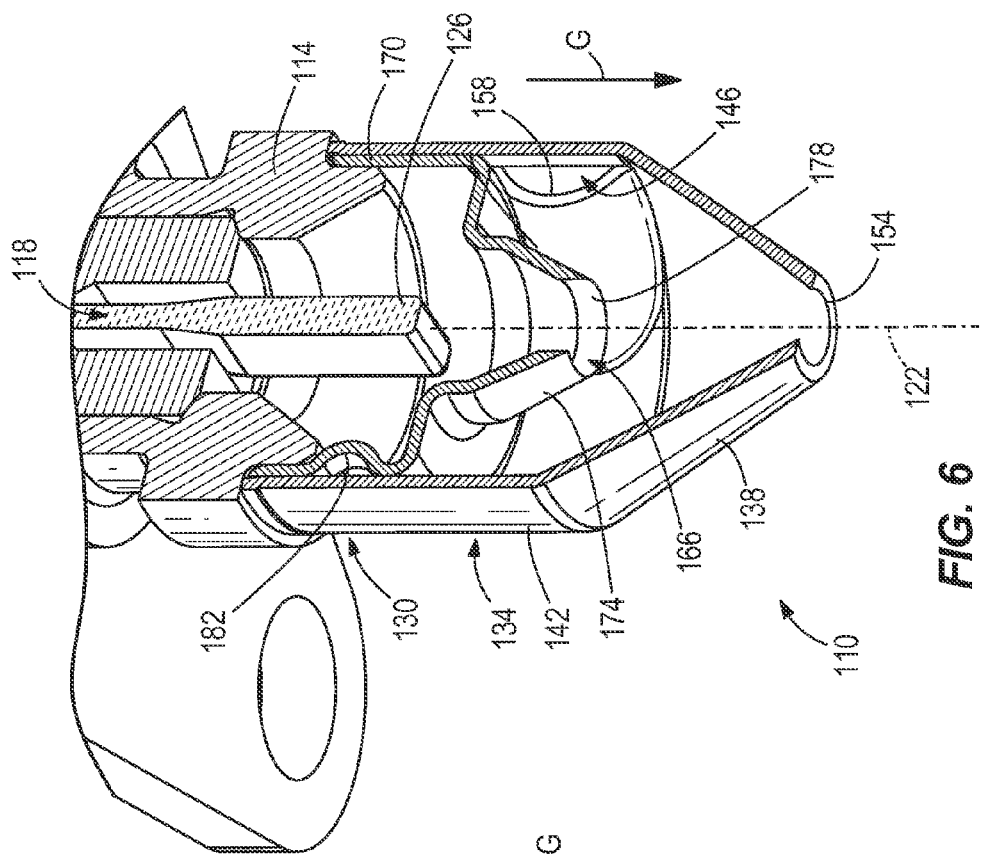
FIG. 6 is a perspective cross-sectional view of the gas sensor of FIG. 5, including an inner tube.
Figure 5:
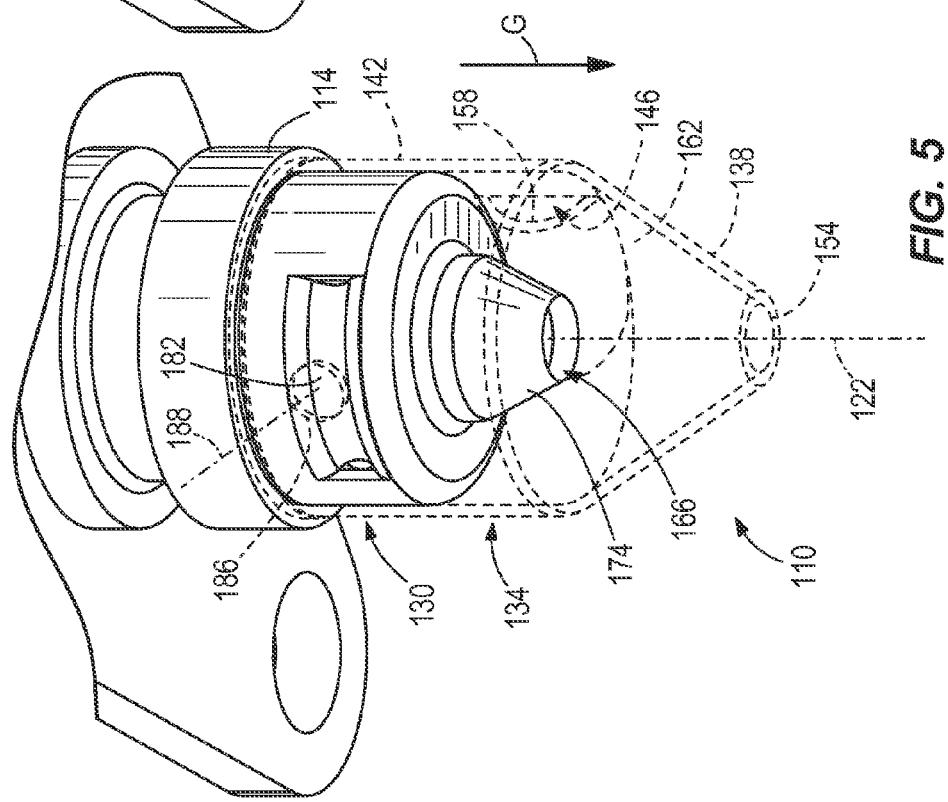
FIG. 5 is a broken-away, perspective view of a gas sensor according to another construction of the invention.
Figure 7:
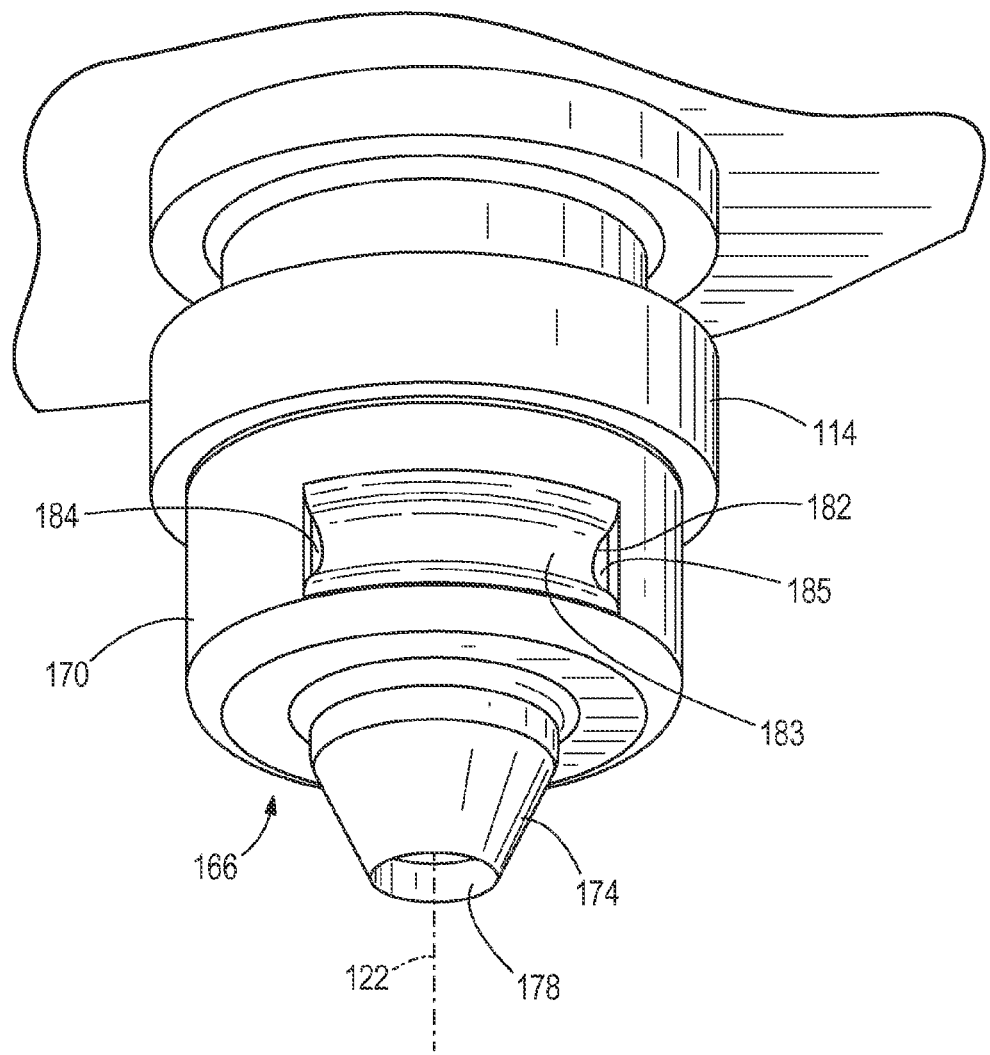
FIG. 7 is a perspective view of the inner tube of FIG. 6.

FIGS. 5-7 illustrate a gas sensor 110 in accordance with another construction. The gas sensor 110 includes a sensor housing 114, and a sensing element 118 located within the sensor housing 114. The sensing element 118 is an oxygen sensing element, although other types of sensing elements 118 are also possible. The sensing element 118 defines an axis 122. The sensing element 118 has a distal end 126 extending from the sensor housing 114. The distal end 126 extends along the axis 122.

The gas sensor 110 further includes a sensor protection element 130. The sensor protection element 130 is coupled to the sensor housing 114. Specifically, the gas sensor protection element 130 is coupled to the sensor housing 114 via a frictional fit over the housing 114, although other forms of coupling are also possible, including attachment with fasteners, brazing, welding, etc. The sensor protection element 130 at least partially surrounds the distal end 126 of the sensing element 118. The sensor protection element 130 controls the flow of gas from outside the sensor protection element 130, into communication with the sensing element 118, and back outside the sensor protection element 130.

The sensor protection element 130 includes an outer tube 134 having a conical portion 138 and a cylindrical portion 142. A gas inlet 146 is located on the cylindrical portion 142. The gas inlet 146 is spaced from the axis 122. The gas inlet 146 is configured to direct gas into the conical portion 138. In particular, the gas inlet 146 is configured to direct gas into the conical portion 138 at an angle such that at least a portion of the gas generates into a swirling vortex within the conical portion 138 (similar to vortex 50 in FIG. 4). The gas entering through gas inlet 146 includes water, particles, and/or other contaminates. With the aid of gravity, the swirling vortex forces the water, particles, and/or other contaminants in the gas toward a waste outlet 154, and inhibits the water, particles, and/or other contaminants from reaching the sensing element 118. The waste outlet 154 is located on the conical portion 138. The axis 122 extends through the waste outlet 154.

The gas inlet 146 illustrated in FIGS. 5-7 has an inwardly facing scoop structure. The inwardly facing scoop structure includes an outer concave surface 158. Gas entering the gas inlet 146 moves along the outer concave surface 158 until the gas is within the conical portion 138. The inwardly facing scoop structure extends toward the axis 122. Gas entering the gas inlet 146 moves along the gas inlet 146 until the gas is within the conical portion 138. The conical portion 138 includes an inner surface 162. The gas entering the gas inlet 146 is directed along the gas inlet 146, and then further along the inner surface 162. The gas inlet 146 directs gas into the conical portion 138 generally tangentially to the inner surface 162.

With continued reference to FIGS. 5-7, the sensor protection element 130 further includes an inner tube 166. The inner tube 166 is disposed within the outer tube 134. The sensing element 118 is located within the inner tube 166. Specifically, the distal end 126 of the sensing element 118 is located within the inner tube 166.

As illustrated in FIG. 6, the inner tube 166 includes a cylindrical portion 170, and a conical portion 174. A gas inlet 178 is located on the conical portion 174 of the inner tube 166. The axis 122 extends through the gas inlet 178. The gas inlet 178 is located generally at or below the gas inlet 146 (the terms "below" and "downward" refer to a direction along axis 22 signified by gravity arrow "G" in FIG. 6), such that any gas that enters through gas inlet 146 must divert downward first prior to entering upward through gas inlet 178. This arrangement of the gas inlets 146, 178 creates a tortuous pathway for gas to reach sensing element 118, and further inhibits water, particles, and/or other contaminants from reaching the sensing element 118.

With continued reference to FIGS. 5-7, the inner tube 166 includes a gas outlet 182. The gas outlet 182 is spaced from the axis 122. The gas outlet 182 is located on the cylindrical portion 170 of the inner tube 166. The gas outlet 182 is disposed on a substantially opposite side of the gas sensor protection element 130 as the gas inlet 146. As illustrated in FIG. 7, the gas outlet 182 is formed as an indented channel 183 along the cylindrical portion 170, with two openings 184, 185 on ends of the indented channel 183. The gas outlet 182 has an elongate structure. The gas outlet 182 extends generally circumferentially along the cylindrical portion 170, about the axis 122.

With reference to FIG. 5, the outer tube 134 further includes a gas outlet 186. The gas outlet 186 is spaced from the axis 122. The gas outlet 186 is located on the cylindrical portion 142 of the outer tube 134 along an axis 188 that extends perpendicular to axis 122. The gas outlet 186 is spaced from and not aligned with the openings 184, 185 of the gas outlet 182 along the axis 188, such that gas within the inner tube 134 must move indirectly from within the inner tube 166 out through the outer tube 134 along a tortuous pathway. This tortuous pathway inhibits water, particles, and/or other contaminants from easily entering the sensor protection element 130 through the gas outlets 182, 186 and contacting the sensing element 118. In the illustrated construction, gas outlet 186 has a circular shape, and gas outlet 182 has an indented channel shape, though other shapes are also possible.

With continued reference to FIGS. 5-7, the gas inlet 146 admits and directs gas into the outer tube 134 in a tangential direction to induce a vortex flow (similar to vortex flow 50 in FIG. 4). Water, particles, and/or other contaminants are driven to the inner wall surface 162 of the outer tube 134 by centrifugal force, and ultimately out through the waste outlet 154. This arrangement inhibits water, particles, and/or other contaminants from reaching the sensing element 118. Thus, only clean gas is admitted into the inner tube 166 through the gas inlet 178. Once the clean gas flows past the sensing element 118, the clean gas exits the sensor protection element 130 through the gas outlets 182, 186. Negative pressure is developed by the gas outlets 182, 186, thereby facilitating the movement of gas flow through the sensor protection element 130.

Additional variations and modifications of the gas sensor protection elements 30, 130 are also possible. For example, in some constructions the sensor protection element 30 includes a gas inlet with an inwardly facing scoop structure (similar to gas inlet 146) located along the conical portion 38 of outer tube 34, rather than the outwardly facing scoop structure of gas inlet 46.

In some constructions the sensor protection element 30 includes non-aligned gas outlets (similar to gas outlets 182, 186) located on the cylindrical portions 70, 42, rather than the directly aligned gas outlets 82, 86.

In some constructions the sensor protection element 130 includes a gas inlet with an outwardly facing scoop structure (similar to gas inlet 46) located on the cylindrical portion 142, rather than the inwardly facing scoop structure of gas inlet 146.

In some constructions the sensor protection element 130 includes directly aligned gas outlets (similar to gas outlets 82, 86) located on the cylindrical portions 170, 142, rather than the non-aligned gas outlets 182, 186.

Various features and advantages of the invention are set forth in the following claims.

What is claimed is:

1. A gas sensor comprising:
   a sensor housing;
   a sensing element located within the sensor housing, the sensing element defining a first axis and having a distal end extending from the sensor housing; and
   a sensor protection element coupled to the sensor housing and at least partially surrounding the distal end of the sensing element, the sensor protection element including:
   an outer tube having a first conical portion, the first conical portion having an inner surface, the outer tube further having a gas inlet, the gas inlet spaced from the first axis, the gas inlet shaped to direct gas into the outer tube to induce a vortex gas flow within the first conical portion of the outer tube, wherein the gas inlet is shaped as one of an outwardly facing scoop structure having an inner concave surface or an inwardly facing scoop structure having an outer concave surface, wherein the gas inlet is configured to direct gas into the first conical portion generally tangentially to the inner surface of the first conical portion, and wherein the outer tube further includes a first gas outlet; and
   an inner tube disposed within the outer tube, wherein the inner tube has a second conical portion that tapers in diameter along the first axis, such that the second conical portion has a diameter that decreases along a direction moving away from the sensing element along the first axis.

2. The gas sensor of claim 1, wherein the gas inlet is on the first conical portion.

3. The gas sensor of claim 1, wherein the sensor protection element further includes a waste outlet located on the first conical portion.

4. The gas sensor of claim 3, wherein the first axis extends through the waste outlet.

5. The gas sensor of claim 1, wherein the outer tube further includes a cylindrical portion.

6. The gas sensor of claim 5, wherein the gas inlet is on the cylindrical portion.

7. The gas sensor of claim 5, wherein the first gas outlet is located on the cylindrical portion.

8. The gas sensor of claim 1, wherein the distal end of the sensing element is located within the inner tube.

9. The gas sensor of claim 1, wherein the gas inlet is a first gas inlet, and the gas sensor protection element further includes a second gas inlet located on the inner tube at a distal end of the second conical portion.

10. The gas sensor of claim 9, wherein the first axis extends through the second gas inlet.

11. The gas sensor of claim 1, wherein the inner tube includes a second gas outlet spaced from the first axis, wherein a second axis extends through at least a portion of both the first gas outlet and the second gas outlet, the second axis extending perpendicular to the first axis.

12. A gas sensor comprising:
   a sensor housing;
   a sensing element located within the sensor housing, the sensing element defining a first axis and having a distal end extending from the sensor housing; and a sensor protection element coupled to the sensor housing and at least partially surrounding the distal end of the sensing element, the sensor protection element including:
- an outer tube having a conical portion;
- a first gas inlet located on the outer tube, the first gas inlet spaced from the first axis;
- a waste outlet located on the conical portion, the first axis extending through the waste outlet;
- an inner tube disposed within the outer tube, the sensing element located within the inner tube;
- a second gas inlet located on the inner tube, the first axis extending through the second gas inlet;
- a first gas outlet located on the inner tube, the first gas outlet spaced from the first axis; and
- a second gas outlet located on the outer tube, the second gas outlet spaced from the first axis, such that a portion of the gas entering the first gas inlet is configured to pass out the waste outlet without passing through the second gas inlet,
- wherein a second axis extends perpendicular to the first axis, the second axis extending through the second gas outlet, and wherein the first gas outlet includes an indented channel defined by a radially inwardly extending indentation of the inner tube, wherein the first gas outlet includes openings on opposite ends of the indented channel, the openings spaced from the second axis and also spaced circumferentially from one another along the inner tube.

13. The gas sensor of claim 12, wherein the second axis extends through at least a portion of both the first gas outlet and second gas outlet.

14. The gas sensor of claim 12, wherein the first gas inlet is shaped to direct gas into the outer tube to induce a vortex gas flow between the outer tube and the inner tube.

15. The gas sensor arrangement of claim 14, wherein the outer tube includes a cylindrical portion, and wherein the first gas inlet is shaped as one of an outwardly facing scoop structure and an inwardly facing scoop structure on the cylindrical portion.

16. The gas sensor arrangement of claim 14, wherein the first gas inlet is shaped as one of an inwardly facing scoop structure and an outwardly facing scoop structure on the conical portion.

17. A gas sensor comprising:
- a sensor housing;
- a sensing element located within the sensor housing, the sensing element defining a first axis and having a distal end extending from the sensor housing; and
- a sensor protection element coupled to the sensor housing and at least partially surrounding the distal end of the sensing element, the sensor protection element including:
  - an outer tube having a first conical portion, the first conical portion having an inner surface, the outer tube further having a gas inlet, the gas inlet spaced from the first axis, the gas inlet shaped to direct gas into the outer tube to induce a vortex gas flow within the first conical portion of the outer tube, wherein the gas inlet is shaped as one of an outwardly facing scoop structure having an inner concave surface or an inwardly facing scoop structure having an outer concave surface, wherein the gas inlet is configured to direct gas into the first conical portion generally tangentially to the inner surface of the first conical portion, and wherein the outer tube further includes a first gas outlet; and
  - an inner tube disposed within the outer tube, wherein the inner tube has a second conical portion, wherein the inner tube includes a second gas outlet spaced from the first axis, wherein a second axis extends through at least a portion of both the first gas outlet and the second gas outlet, the second axis extending perpendicular to the first axis.

18. The gas sensor arrangement of claim 17, wherein the outer tube includes a cylindrical portion.

19. The gas sensor arrangement of claim 17, wherein the sensor protection element further includes a waste outlet located on the first conical portion.

20. The gas sensor of claim 19, wherein the first axis extends through the waste outlet.

* * * * *